United States Patent
Nguyen et al.

(10) Patent No.: US 10,230,216 B1
(45) Date of Patent: Mar. 12, 2019

(54) TUNABLE MULTI-FREQUENCY TERAHERTZ QUANTUM CASCADE LASER SOURCE

(71) Applicant: The United States of America as represented by the Administrator of the National Aeronautics and Space Administration, Washington, DC (US)

(72) Inventors: Hung D. Nguyen, Lakewood, OH (US); Rainee N. Simons, North Olmsted, OH (US); Edwin G. Wintucky, Eastlake, OH (US)

(73) Assignee: The United States of America as Represented by the Admin of the National Aeronautics and Space Administration, Washington, DC (US)

( * ) Notice: Subject to any disclaimer, the term of this patent is extended or adjusted under 35 U.S.C. 154(b) by 966 days.

(21) Appl. No.: 14/698,050

(22) Filed: Apr. 28, 2015

Related U.S. Application Data (60) Provisional application No. 61/987,580, filed on May 2, 2014.

(51) Int. Cl.
| | |
|---|---|
| *H01S 5/34* | (2006.01) |
| *G02B 6/12* | (2006.01) |
| *H04J 14/02* | (2006.01) |
| *H04Q 11/00* | (2006.01) |
| *G01N 21/3581* | (2014.01) |

(52) U.S. Cl.
CPC ........ *H01S 5/3401* (2013.01); *G02B 6/12011* (2013.01); *H04J 14/0267* (2013.01); *G01N 21/3581* (2013.01); *G02F 2203/13* (2013.01); *H01S 2302/02* (2013.01); *H04Q 2011/0016* (2013.01)

(58) Field of Classification Search
CPC .................................................. H01S 2302/02
See application file for complete search history.

(56) References Cited

U.S. PATENT DOCUMENTS

| | | | |
|---|---|---|---|
| 7,826,509 B2 | 11/2010 | Belkin et al. | |
| 7,974,325 B2 | 7/2011 | Belkin et al. | |
| 8,619,832 B2 | 12/2013 | Hu et al. | |
| 9,525,492 B2 * | 12/2016 | Duan | H01S 5/0612 |
| 2003/0011840 A1 * | 1/2003 | Mitra | H01S 3/2383 398/79 |
| 2005/0271093 A1 * | 12/2005 | Wang | H04B 10/508 372/25 |
| 2008/0304531 A1 | 12/2008 | Mansour et al. | |
| 2011/0058176 A1 | 3/2011 | Pflugl et al. | |

(Continued)

*Primary Examiner* — Jerry Rahll
(74) *Attorney, Agent, or Firm* — Robert H. Earp, III; William M. Johnson (57) ABSTRACT

A tunable QCL source that utilizes a full bandwidth of a broadband THz QCL, and produces a significantly large number of frequency channels, is provided. The tunable QCL source includes a grating router configured to receive a terahertz frequency from a tunable quantum cascade laser and generate a plurality of terahertz frequencies. The tunable QCL source also includes a waveguide controller configured to receive the plurality of terahertz frequencies from the grating router, and select a desired terahertz frequency from the plurality of terahertz frequencies to be outputted by a waveguide multiplexer.

19 Claims, 7 Drawing Sheets

(56) References Cited

U.S. PATENT DOCUMENTS

| | | | |
|---|---|---|---|
| 2011/0129192 A1* | 6/2011 | Shen | H01L 23/38 |
| | | | 385/134 |
| 2012/0008140 A1* | 1/2012 | Khan | G01N 21/3581 |
| | | | 356/326 |
| 2012/0033697 A1 | 2/2012 | Goyal et al. | |
| 2013/0121359 A1 | 5/2013 | Mansour et al. | |
| 2013/0148678 A1 | 6/2013 | Diehl et al. | |
| 2013/0208743 A1 | 8/2013 | Capasso et al. | |
| 2013/0286397 A1 | 10/2013 | Witinski et al. | |
| 2015/0236793 A1* | 8/2015 | Duan | H04B 10/572 |
| | | | 398/28 |
| 2016/0109655 A1* | 4/2016 | Vurgaftman | G02B 6/122 |
| | | | 385/14 |

\* cited by examiner

TUNABLE MULTI-FREQUENCY TERAHERTZ QUANTUM CASCADE LASER SOURCE

CROSS REFERENCE TO RELATED APPLICATION

This application claims the benefit of U.S. Provisional Patent Application Ser. No. 61/987,580, which was filed May 2, 2014. The subject matter of this earlier-filed application is hereby incorporated by reference in its entirety.

ORIGIN OF THE INVENTION

The invention described herein was made by employees of the United States Government and may be manufactured and used by or for the Government for Government purposes without the payment of any royalties thereon or therefore.

FIELD

The present invention generally pertains to a tunable laser source, and in particular, to a tunable multi-frequency terahertz quantum cascade laser source.

BACKGROUND

Interest in the use of terahertz (THz) detectors outside of a laboratory for space, atmospheric, and terrestrial applications has grown immensely in the past half century. Of particular interest in recent years is the development of a quantum cascade laser (QCL) as a THz frequency source. Attractive features of the THz QCL include high output power (greater than 100 mW), a good wall-plug efficiency, spectral purity, stability, compactness, and reliability. A QCL operating in the range of 1.2 to 4.9 THz has been demonstrated. A multimode QCL can be designed to operate at frequency below 1.2 THz. However, accurate and reliable tuning of the QCL emission to select one or more single-mode frequencies is essential for most applications and is still an issue.

A number of approaches for tuning the emission from a THz QCL, which may use temperature, electrical (current/voltage), resonant cavity or mechanical methods for frequency and mode selection, are currently being investigated. All of these approaches have one or more negative features. For example, these approaches limit range of tuning, have high cost, are very complex, and lack thermal and vibrational stability. These limitations adversely affect commercialization and use in a large variety of potential applications such as remote sensing, spectroscopy, heterodyne receiver, security screening, and bio-medicine.

Thus, an alternative approach may be beneficial.

SUMMARY

Certain embodiments of the present invention may be implemented and provide solutions to the problems and needs in the art that have not yet been fully solved by conventional tuning approaches for THz QCL. For example, some embodiments pertain to a tunable QCL source that utilizes a full bandwidth of a broadband THz QCL, and produces a significantly large number of frequency channels without any of the above-mentioned shortcomings.

In one embodiment, an apparatus includes a grating router configured to receive a terahertz frequency from a tunable quantum cascade laser and generate a plurality of terahertz frequencies. The apparatus also includes a waveguide controller configured to receive the plurality of terahertz frequencies from the grating router, and select a desired terahertz frequency from the plurality of terahertz frequencies to be outputted by a waveguide multiplexer.

In another embodiment, an apparatus includes a tunable terahertz quantum cascade laser source configured to produce a plurality of terahertz frequencies, and output a desired terahertz frequency from the plurality of terahertz frequencies.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE EMBODIMENTS

Some embodiments of the present invention pertain to a novel high resolution QCL emission tuning approach and systems for tuning a multi-frequency THZ QCL source. In some embodiments, the high resolution QCL emission tuning approach avoids the limitations of the other tuning approaches discussed above and includes the benefits of a significantly larger number of frequency channels. The high resolution QCL emission tuning approach reduces the size, weight, complexity, and cost of a tunable THz receiver and also increases the thermal and vibrational stability.

Figure 1:
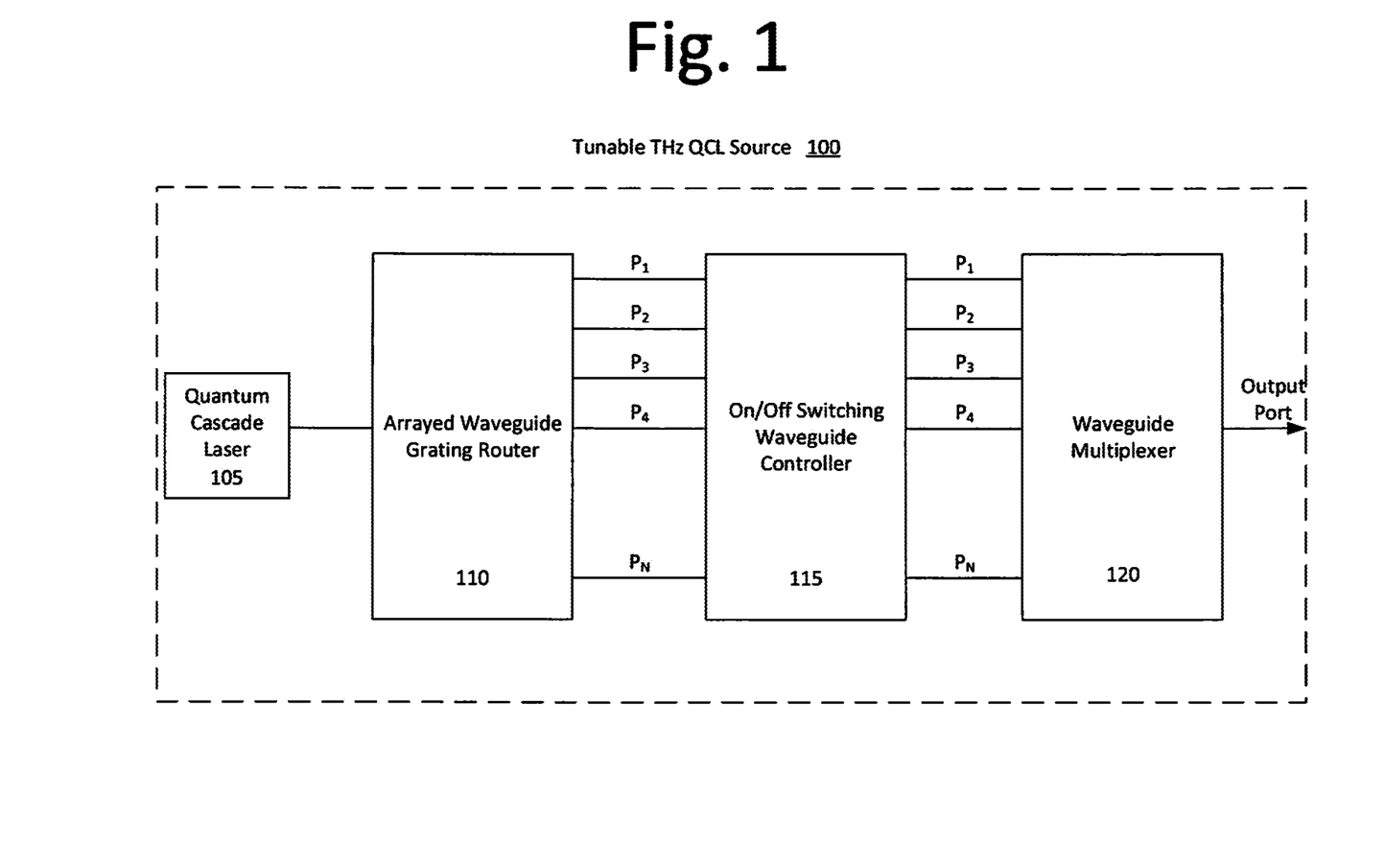
FIG. 1 is a block diagram illustrating a tunable THz source based on a QCL, according to an embodiment of the present invention.

FIG. 1 is a block diagram illustrating a tunable THz source 100 based on a QCL 105, according to an embodiment of the present invention. In this embodiment, QCL 105 may generate THz frequencies that are fed into grating router 110. For purposes of explanation, a center frequency of 1.5 THz has been selected. However, it should be appreciated that the center frequency may operate at any THz frequency. Grating router 110 may include a patterned array of curved waveguide channels formed on a semiconductor substrate. See, for example, FIG. 2 for a more detailed explanation of grating router 110. The patterned array of curved waveguide channels may be configured according to a predetermined difference in path lengths and separation between adjacent waveguides. The difference in path lengths may introduce phase delays that result in producing different single-mode frequencies at the output ports of grating router 110. For example, with a center frequency of 1.5 THz, the following single-mode frequencies may be produced at $P_1$=1.46 THz, $P_2$=1.48 THz, $P_3$=1.50 THz, $P_4$=1.52 THz . . . $P_N$=N THz, N is any arbitrary number.

These output frequencies may be fed into waveguide controller 115, which is configured in some embodiments to select a desired frequency. In one embodiment, waveguide controller 115 may be a matched array of rectangular waveguide structures formed using a non-linear material. See FIGS. 4, 5A, and 5B for a more detailed explanation of waveguide controller 115.

The desired frequency may then be fed into waveguide multiplexer 120. For purposes of explanation, if path $P_2$ in FIG. 1 is selected as the desired frequency, e.g., 1.48 THz, then all other paths $P_1$, $P_3$ . . . $P_N$ from waveguide controller 115 are shut off. This allows the 1.48 THz on path $P_2$ in this example to be fed into waveguide multiplexer 120. Waveguide multiplexer 120 may combine the output ports of waveguide controller 115 into a single output for transmission, such that the desired frequency is outputted.

Figure 2:
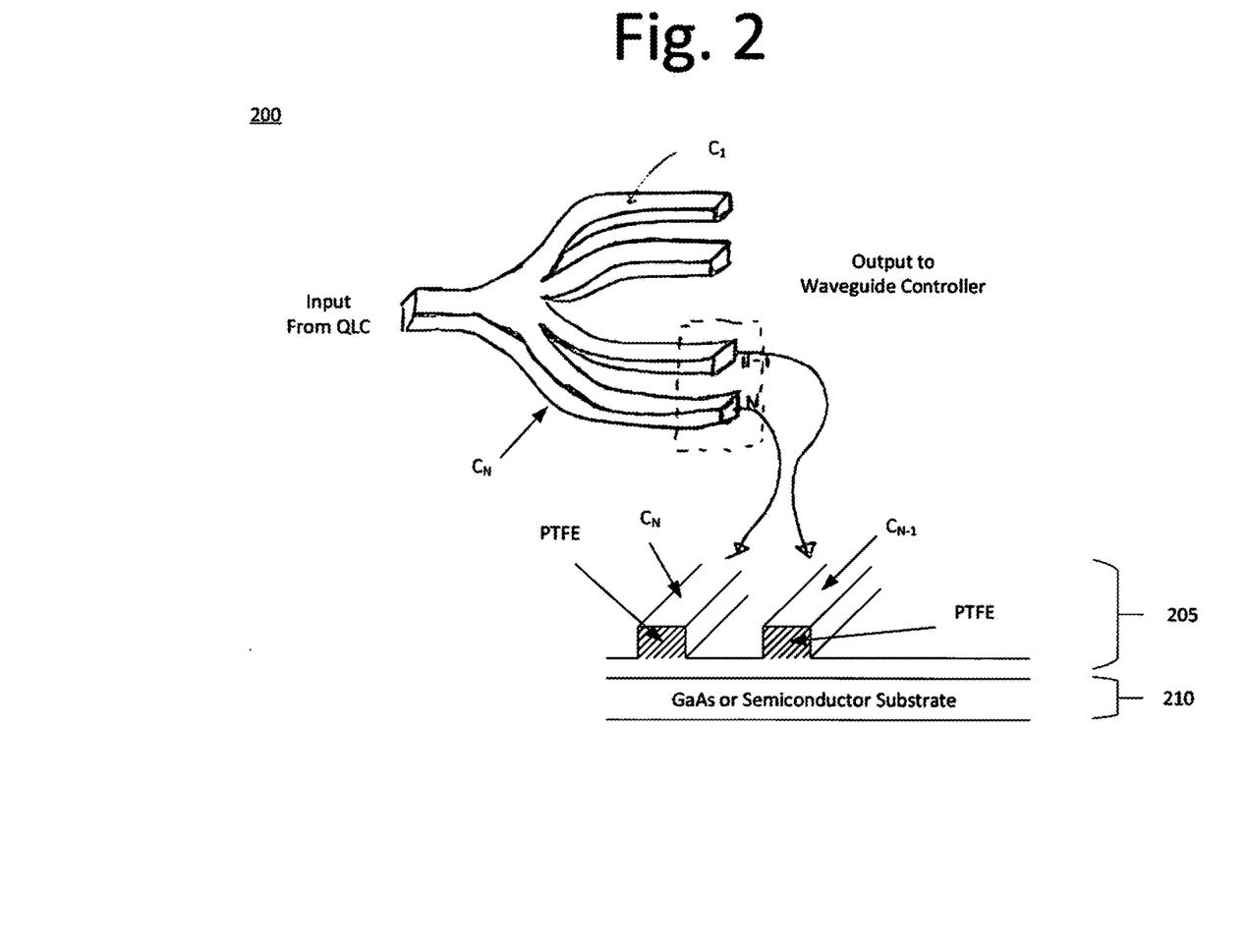
FIG. 2 illustrates a structure of an arrayed waveguide grating router configured and fabricated using polytetrafluoroethylene (PTFE) to operate in THz frequency range (hereinafter "grating router"), according to an embodiment of the present invention.

FIG. 2 illustrates a structure of grating router 200, according to an embodiment of the present invention. Many conventional waveguide grating routers operate across the 1.3 micron to 1.550 micron wavelength in optical infrared spectrum. In some embodiments, however, the capability of grating router 200 may be extended to operate from 60 micron wavelength (5 THz frequency) to 300 micron wavelength (1 THz frequency).

In this embodiment, grating router 200 may include a patterned array of curved waveguide channels $C_1$ . . . $C_N$ formed on a semiconductor substrate 210, and configured (or calibrated) according to a predetermined difference in path length and separation between adjacent waveguides. The difference in waveguide path lengths may introduce phase delays resulting in production of different single-mode frequencies at the output ports of grating router 200. For purposes of explanation examples of frequencies being 1.46 THz, 1.48 THz, 1.50 Hz, 1.52 THz . . . N THz, N is any arbitrary number.

Grating router 200, including waveguide channels $C_1$ . . . $C_N$, may be fabricated using PTFE, and may be etched to form ridged waveguide structure 205. In some embodiments, ridged waveguide structure 205 may be deposited on top of semiconductor substrate 210, which may include, but is not limited, to gallium arsenide (GaAs). In other embodiments, other semiconductor materials may be used. The use of the PTFE has the property of transparency of THz, resulting in producing a very low loss signal at the THz frequency range.

Figure 3:
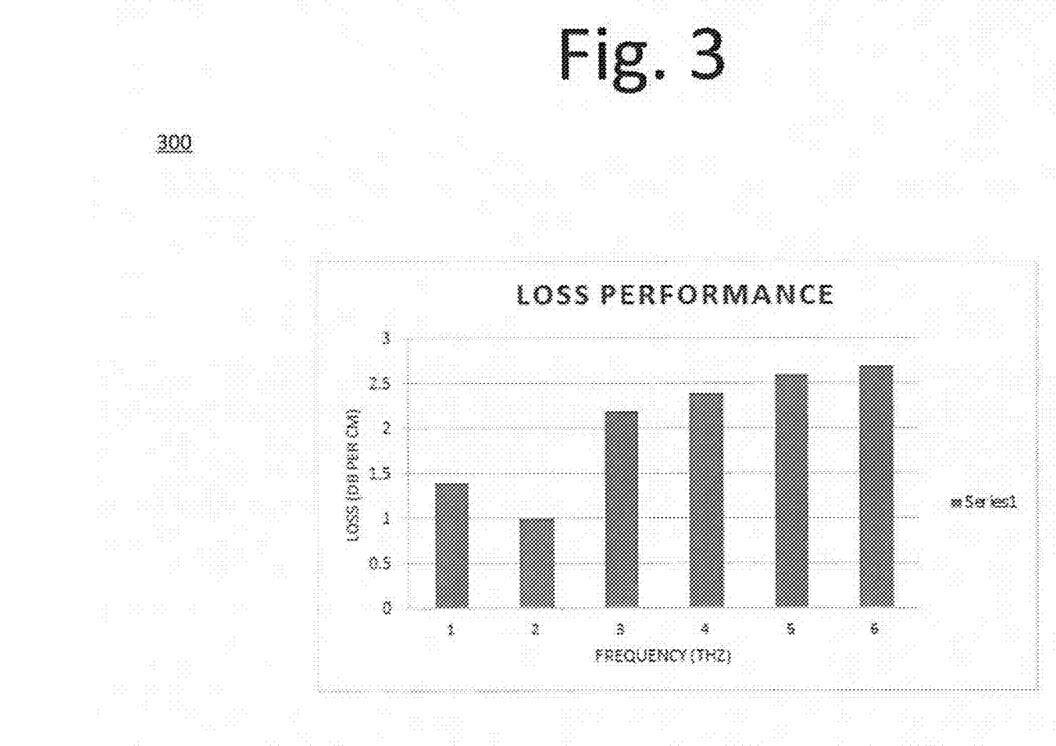
FIG. 3 is a graph illustrating a loss performance of PTFE, according to an embodiment of the present invention.
Figure 4:
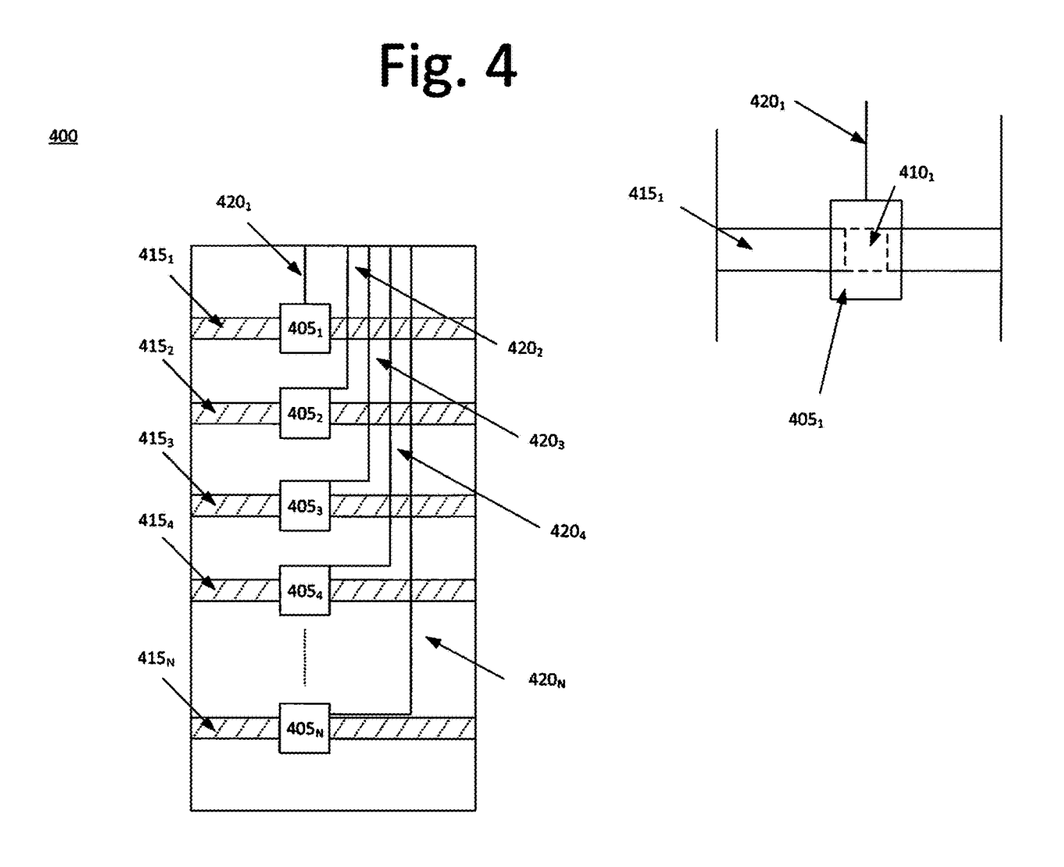
FIG. 4 is a block diagram illustrating an on/off switching waveguide controller (hereinafter "waveguide controller"), according to an embodiment of the present invention.

FIG. 3 is a graph 300 illustrating a loss performance of ridged waveguide structure fabricated using PTFE material, according to an embodiment of the present invention. In this embodiment, FIG. 3 illustrates the loss (dB per cm) corresponding to a range of frequencies from 1 to 6 THz. For example, when the frequency is at 1 THz, the PTFE waveguide may suffer 1.4 dB per cm. In another example, when the frequency is at 2 THz, the PTFE waveguide may suffer 1 dB per cm loss, and so on FIG. 4 is a block diagram illustrating waveguide controller 400, according to an embodiment of the present invention. In this embodiment, waveguide controller 400 includes an array of waveguide elements, each waveguide element having a patch electrode $405_1$ . . . $405_N$, a non-linear waveguide $410_1$ . . . $410_N$, a linear waveguide $415_1$ . . . $415_N$, and a wire $420_1$ . . . $420_N$ connecting patch electrode $405_1$ . . . $405_N$ with the electronic control processor (not shown). The nonlinear waveguide material in some embodiments is polymethylmethacrylate (PMMA).

Figure 5A:
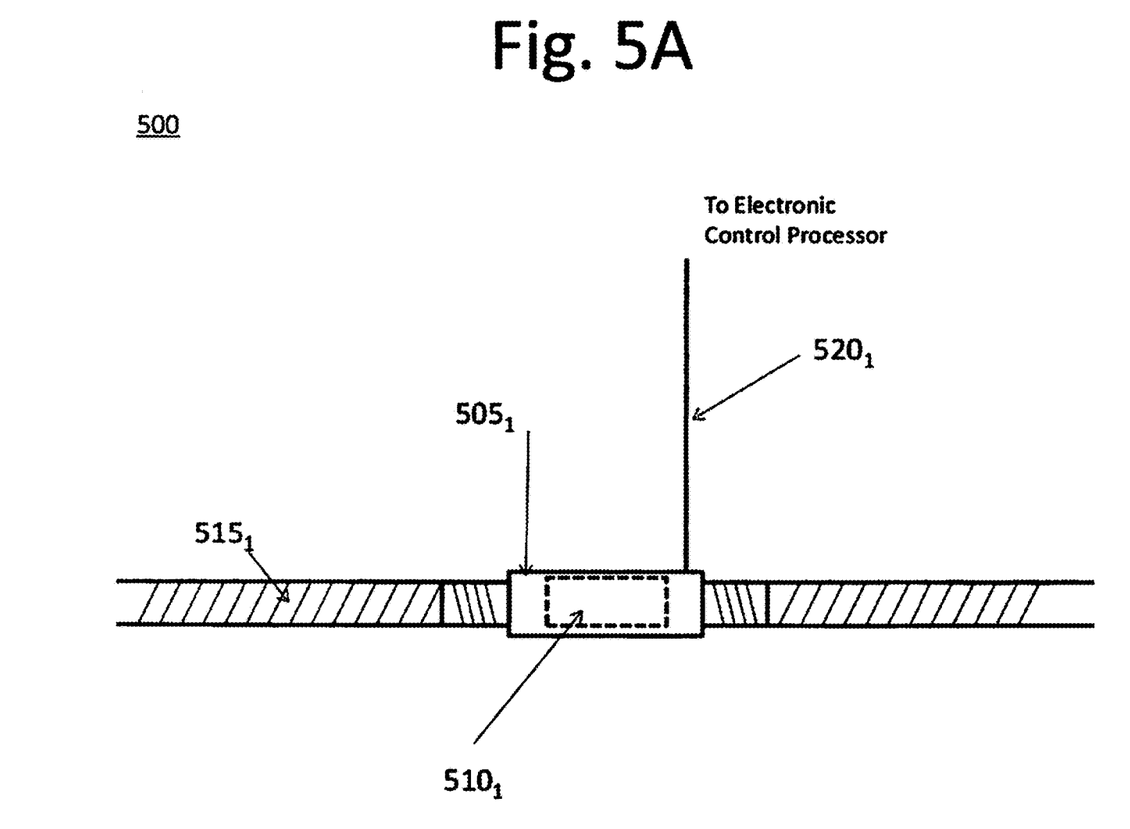
FIG. 5A illustrates a top view of a single element in an array of the waveguide controller, according to an embodiment of the present invention.
Figure 5B:
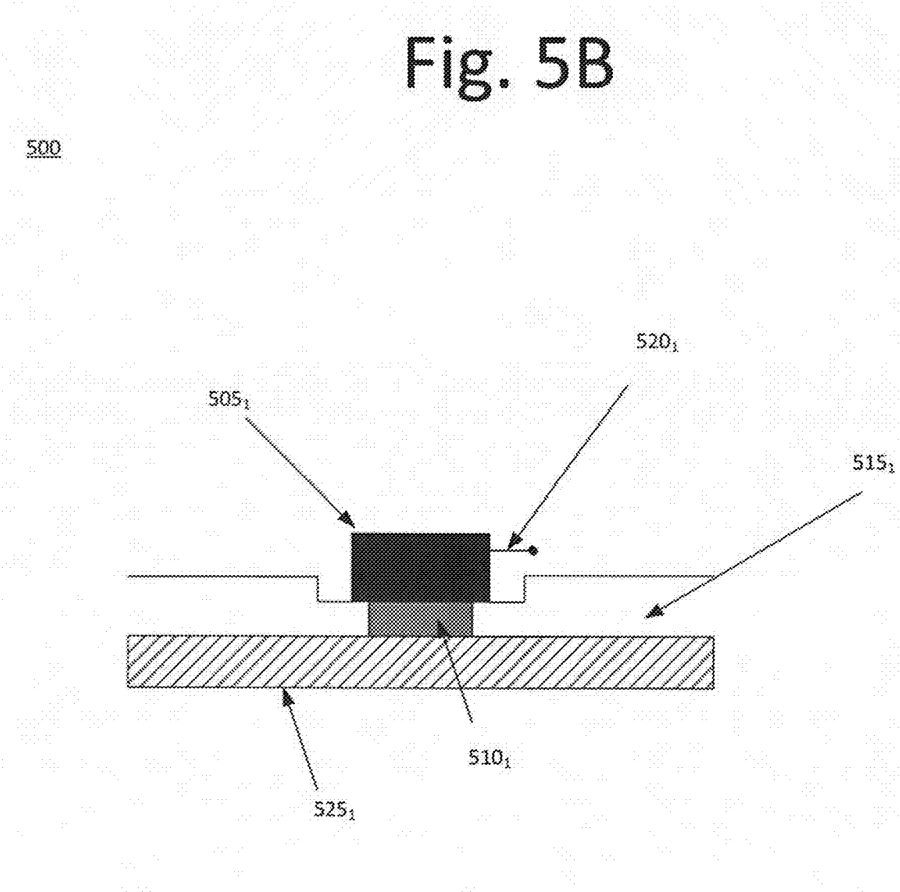
FIG. 5B illustrates a side view of a single element in an array of the waveguide controller, according to an embodiment of the present invention.

As discussed above, output frequencies from the grating router are fed into waveguide controller 400 to enable selection of the desired frequency. In this embodiment, waveguide controller 400 may be a matched array of rectangular waveguide structures formed using a nonlinear material. The top and side view of a single element in an array is shown in FIG. 5A and FIG. 5B, respectively. In this example, patch electrodes $505_1$ . . . $505_N$ may be fabricated on top of non-linear waveguides $510_1$ . . . $510_N$, and may function as a switching mechanism. Patch electrodes $505_1$ . . . $505_N$ may be individually connected to an electronic control processor (not shown) via circuit wires $520_1$ . . . $520_N$. The electronic control processor may turn ON and OFF any one of non-linear waveguides $510_1$ . . . $510_N$ independently to permit selection of the desired frequency signal passing through any one of linear waveguides $515_1$ . . . $515_N$.

FIGS. 5A and 5B illustrate a top view and side view of waveguide controller 500, according to an embodiment of the present invention. In this embodiment, non-linear waveguide $510_1$ is located on top of wafer 525, and may be made of PMMA. A patch-type electrode $505_1$ may be fabricated on top of non-linear waveguide $510_1$. A circuit wire $520_1$ may connect patch-type electrode $505_1$ with an electronic control processor (not shown) to permit selection of the desired THz frequency passing through linear waveguide $515_1$, which is also located on wafer 525 in this embodiment.

Figure 6:
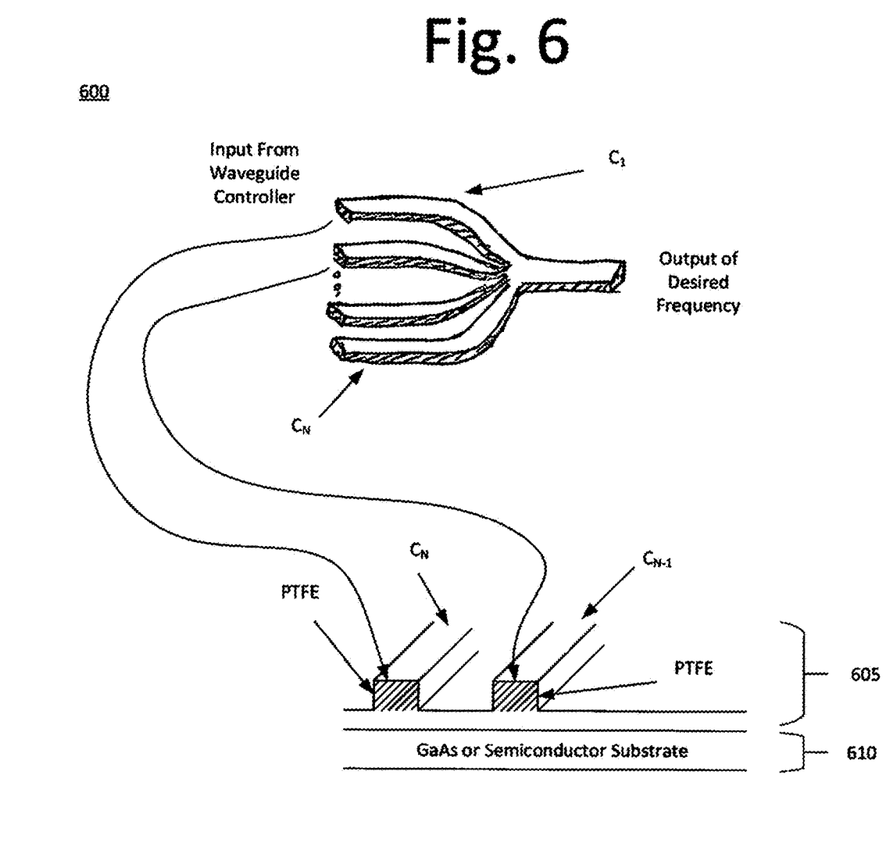
FIG. 6 illustrates a waveguide multiplexer configured and fabricated using PTFE to operate in THz frequency range, according to an embodiment of the present invention.

FIG. 6 illustrates a waveguide multiplexer 600, according to an embodiment of the present invention. As discussed above, the outputs of the waveguide controller are fed into waveguide multiplexer 600. Waveguide multiplexer 600 in some embodiments includes multiple channels $C_1$ . . . $C_N$ and combines the channels into a single output. It should be appreciated that any one of multiple channels $C_1$ . . . $C_N$ may carry the desired THz frequency. Waveguide multiplexer 600 may be fabricated from PTFE, which is transparent to THz spectrum, and may be etched to form a ridged waveguide structure 605. Ridged waveguide structure 605 may be deposited on top of substrate 610 comprising GaAs or any other semiconductor substrate in some embodiments.

In some embodiments, a tunable THz QCL source, i.e., 1-5 THz, is based on a passive waveguide tuning mechanism. The passive waveguide tuning mechanism may utilize a full bandwidth of a broadband THz QCL and produce a significantly large number of frequency channels without any of the above-mentioned shortcomings. The tunable THz QCL source may be coupled to a grating router. The grating router may include a linear dielectric waveguide array configured to generate a high density of THz channels. The output of the grating router may enter an on/off switching non-linear waveguide controller to enable selection of a desired single mode frequency. The outputs of the waveguide controller are combined into a signal using a multiplexer.

It will be readily understood that the components of various embodiments of the present invention, as generally described and illustrated in the figures herein, may be arranged and designed in a wide variety of different configurations. Thus, the detailed description of the embodiments, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. An apparatus, comprising:
a grating router configured to receive a terahertz frequency from a tunable quantum cascade laser and generate a plurality of terahertz frequencies; and
a waveguide controller configured to receive the plurality of terahertz frequencies from the grating router, and select a desired terahertz frequency from the plurality of terahertz frequencies to be outputted by a waveguide multiplexer.

2. The apparatus of claim 1, wherein the grating router comprises:
a plurality of waveguide channels formed on a semiconductor substrate to allow the plurality of terahertz frequencies to be generated.

3. The apparatus of claim 2, wherein the plurality of waveguide channels are calibrated according to a predetermined difference in path length and a separation between adjacent waveguides.

4. The apparatus of claim 2, wherein the plurality of waveguide channels are fabricated from polytetrafluoroethylene allowing each of the plurality of waveguide channels operate in a terahertz frequency range.

5. The apparatus of claim 4, wherein the semiconductor substrate comprises gallium arsenide.

6. The apparatus of claim 1, wherein the waveguide controller comprises array of waveguide elements allowing a control processor to select the desired terahertz frequency from the plurality of terahertz frequencies.

7. The apparatus of claim 6, wherein each waveguide element in the array of waveguide elements comprises a patch electrode fabricated on top of a non-linear waveguide, and is connected to the control processor to enable selection of the desired terahertz frequency from the plurality of terahertz frequencies.

8. The apparatus of claim 7, wherein the non-linear waveguide comprises polymethylmethacrylate.

9. The apparatus of claim 7, wherein each waveguide element in the array of waveguide elements further comprises a circuit wire connecting the patch electrode to the control processor to enable selection of the desired terahertz frequency from the plurality of terahertz frequencies.

10. The apparatus of claim 1, wherein the waveguide multiplexer comprises a plurality of waveguide channels, wherein one of the plurality of waveguide channels is configured to emit the desired terahertz frequency to be outputted.

11. The apparatus of claim 10, wherein each of the plurality of waveguide channels are fabricated from polytetrafluoroethylene.

12. The apparatus of claim 10, wherein each of the plurality of waveguide channels are formed on a semiconductor substrate.

13. The apparatus of claim 12, wherein the semiconductor substrate comprises gallium arsenide.

14. An apparatus, comprising:
a tunable terahertz quantum cascade laser source configured to produce a plurality of terahertz frequencies, and output a desired terahertz frequency from the plurality of terahertz frequencies.

15. The apparatus of claim 14, wherein the tunable terahertz quantum cascade laser source comprises
a grating router with patterned array of curved waveguide channels formed on a semiconductor substrate and calibrated according to a predetermined difference in path length and separation between adjacent waveguides.

16. The apparatus of claim 15, wherein the patterned array of curved waveguide channels are fabricated from polytetrafluoroethylene.

17. The apparatus of claim 14, wherein the tunable terahertz quantum cascade laser source comprises a waveguide controller to select the desired terahertz frequency from the plurality of terahertz frequencies.

18. The apparatus of claim 17, wherein the tunable terahertz quantum cascade laser source comprises a waveguide multiplexer configured to combine outputs of the waveguide controller into a single output for transmission, such that the desired frequency is outputted.

19. The apparatus of claim 18, wherein the waveguide multiplexer comprises a patterned array of curved waveguide channels formed on a semiconductor substrate, wherein the patterned array of curved waveguide channels are fabricated from polytetrafluoroethylene.

* * * * *